United States Patent [19]
Harrawood et al.

[11] Patent Number: 5,386,453
[45] Date of Patent: Jan. 31, 1995

[54] IMAGING AND TREATMENT APPARATUS HAVING A FLOOR-MOUNTED GUIDING TRACK

[75] Inventors: Larry E. Harrawood, Sandy; James R. Harvey, Salt Lake City, both of Utah

[73] Assignee: Diasonics, Inc., Milpitas, Calif.

[21] Appl. No.: 881,771

[22] Filed: May 12, 1992

[51] Int. Cl.6 ............................................. H05G 1/02
[52] U.S. Cl. .................................... 378/196; 378/198; 378/193
[58] Field of Search ............... 378/196, 197, 193, 208, 378/209, 198, 195; 5/607, 608

[56] References Cited

U.S. PATENT DOCUMENTS

| | | | |
|---|---|---|---|
| 3,281,598 | 10/1966 | Hollstein | 250/57 |
| 4,426,725 | 1/1984 | Grady | 378/196 |
| 4,649,560 | 3/1987 | Grady et al. | 378/196 |
| 4,727,564 | 2/1988 | Mekker et al. | 378/197 |
| 4,928,283 | 5/1990 | Gordon | 378/196 |
| 4,955,046 | 9/1990 | Siczek et al. | 378/197 |
| 4,979,202 | 12/1990 | Siczek et al. | 378/196 |
| 4,987,583 | 1/1991 | Travanty et al. | 378/91 |
| 4,989,228 | 1/1991 | Louiday | 378/196 |
| 5,014,292 | 5/1991 | Siczck et al. | 378/196 |
| 5,081,661 | 1/1992 | Larsson | 378/196 |
| 5,131,105 | 7/1992 | Harrawood et al. | 5/607 |
| 5,230,112 | 7/1993 | Harrawood et al. | 5/607 |

OTHER PUBLICATIONS

Advertisement for an x-ray system for whole body examination and angiography in interventional procedures, Siemens Ag, Germany (undated).
Advertisement for an angiography whole body system, Shimadzu Europa GmbH, Germany (undated).
Marketing brochure entitled "Intraoperative Angiographic/Surgical Table, Model 206," Angiographic Devices Corp., Littleton, Mass. (undated but published in 1987).
Advertisement regarding the KOORDINATS brand system (undated).
Product literature on the DIAGNOST EP 9000 System, Philips Medical Systems (Jan. 1990).
Product literature on the DIAGNOST EP 8000 Electrophysiology System, Philips Medical Systems (Sep. 1990).

*Primary Examiner*—David P. Porta
*Assistant Examiner*—Kim-Kwok Chu
*Attorney, Agent, or Firm*—Blakely, Sokoloff, Taylor & Zafman

[57] ABSTRACT

An apparatus having a support for supporting a subject on a surface and an imager for imaging the subject. The imager is movably coupled to a track to allow relative movement of the imager about the support. The track is located substantially along a plane which is substantially parallel to the surface of the support. The support may, in some embodiments, be rotatable from a horizontal to a vertical position for certain procedures. The track provides movement of the imager about at least three sides of the apparatus and, in some embodiments, is affixed to the floor. Further, the track is substantially aligned with a centerline of the support surface. This provides a firm support for the imaging means, but keeps the support structure at a position where it will not interfere with clinical operations.

53 Claims, 9 Drawing Sheets

IMAGING AND TREATMENT APPARATUS HAVING A FLOOR-MOUNTED GUIDING TRACK

BACKGROUND OF THE INVENTION

1. Field of the Invention

The present invention relates to imaging and treatment apparatus. More specifically, the present invention relates to an imaging and treatment apparatus which uses a rail or track for mounting of the imaging and treatment apparatus which is generally aligned with the centerline of a subject support.

2. Background of Related Information

Various types of imaging apparatus are well-known in the medical arts. Such imaging apparatus includes "U-arm" imaging apparatus which provide various angles of imagery of a living subject typically situated on a table top or other supporting means. Once such prior art apparatus was described in U.S. Pat. No. 3,281,598, dated Oct. 25, 1966, entitled "Overhead Support For A Vertically and Rotatably Movable X-ray Tube Support Arm and Cooperating Tiltable X-ray Table" of Oswald C. Hollstein ("Hollstein"). Such apparatus typically provides a variety of angles at which a subject may be imaged in order to obtain X-ray projections perpendicular to blood vessels under examination. This allows for better imagery of the blood vessels, and the movement provides for flexibility of the imaging system. Such apparatus typically provide a system which is especially useful in electrophysiology treatments of heart arrythmias and other ailments requiring angiographic studies. Such apparatus includes a supporting table for a subject which provides the ability to administer medication to the subject while lying in a horizontal position and rotate the supporting table to a substantially vertically position, thus monitoring the effectiveness of the medication. Such apparatus includes the ability to quickly lower the subject to a horizontal position once again, if syncope occurs.

One shortcoming of certain prior art systems, including Hollstein, is that these systems require a mounting apparatus for the "C-arm" or "U-arm" imaging apparatus which, in some systems, is affixed to the ceiling. For instance, in Hollstein, substantial coupling means are present in the system in order to provide a rigid support for the imaging apparatus in relation to the support apparatus for the subject. The shortcoming of the ceiling mounted system is that extensive structure is required in the ceiling of the examination room, thus requiring extensive modifications to existing structures which can be very expensive and may be impractical in some circumstances. Because the weight of such imaging apparatus is substantial, such structure may not be possible in certain clinical environments. In addition, the overhead mounting apparatus tends to be complicated, requiring multiple parallel rails or other extensive support structure to support the weight of the imaging system.

Another disadvantage of this system is due to the extensive overhead ceiling structures, debris has the tendency to collect in the support structure and, if not maintained properly, may discharge the debris onto the subject. Of course, this is not desirable in a clinical environment. Another disadvantage of the prior art systems, such as Hollstein, require extensive articulated arms which extend from the ceiling and, in order to preserve the required motion in an examination room which has a very high ceiling, the arms coupled to the C-arm system are required to be very long. In such a system, oscillations due to the length of the arms may be significant, thus adversely affecting the images obtained in the system.

A second type of system is that which utilizes floor mounted rails or guides along the side of the table. In this manner, the X-ray unit may traverse along the length of the table, thus providing imaging along the full length of the subject situated on the table. Generally, however, these systems do not have the capability to image from one and/or the opposite side of the table in order to provide a full range of positions at which to image blood vessels. The capability to image blood vessels from various angles is desirable because a perpendicular view of the vessel provides the highest quality possible image. Prior art floor mounted systems generally lack the capability of imaging from more than a single side of the subject.

Yet another prior art approach is the use of a portable C-arm X-ray imaging unit. Once such unit was described in U.S. Pat. No. 4,955,046, issued Sep. 4, 1990, entitled "C-arm For X-ray Diagnostic Examination" of Siczek et al. ("Siczek"). Siczek describes an L-arm mounted on a portable unit having wheels, with a C-arm attached to the L-arm. This portable unit allows the unit to be wheeled around to various locations as the clinical personnel desires. The main disadvantage of this system is that the movements of the arm along the longitudinal axis of the support table is not provided, thus precise movements of the C-arm must be done manually. Also, repetition of movements is not possible because the imaging apparatus is not mounted in some way in relation to the table upon which the patient is supported. Precise and repetitive movements are difficult if not impossible tasks.

Furthermore, prior art apparatus such as Siczek require extensive peripheral equipment (such as generators, monitors, etc.) which make movement of the apparatus cumbersome and difficult. Also, scheduling of portable units becomes problematic due to the high demand for such devices in a variety of situations. In summary, dedicated, fixed installation of X-ray equipment is desirable for certain applications such as electrophysiology procedures. Yet another disadvantage of the prior art, including Siczek, is that longitudinal motion of the imaging apparatus along the length of the table is manual and, therefore, poses problems for the clinician, who is in a sterile condition. It would be advantageous to move the imaging apparatus by means of a motorized control, activated from a control console which is in a sterilized condition, such as covered with a sterile drape. Prior art apparatus, and as Siczek, sometimes use floating tabletops for placement of the patient to solve these problems, however, such apparatus suffer from some inherent problems. For example, for applications such as electrophysiology treatments which require a tiltable patient support, the floating tabletop must be locked prior to rotation. If the table is not locked during rotation, the top will slide and the patient may be injured. To ensure safety of operation, the clinician must lock the floating tabletop prior to rotation, an extra consideration which may be overlooked during treatment.

Another disadvantage of portable X-ray imaging apparatus such as Siczek is that the L-arm must be positioned at an approximate 22.5 degree angle with respect to the plane of the support table. This is to allow the C-arm to have the full range of motion of ±45 degrees of rotation with respect to the table upon which the patient is resting. This offsets the body of the C-arm and causes the entire apparatus to consume more space than would be consumed by a fixed system specifically designed for the clinical procedures being performed.

Yet another prior art system uses a combination of a ceiling mounted track and a floor mounted track. In this manner, the "L-arm" apparatus has been eliminated and replaced with a vertical pole extending from the floor to the ceiling. As discussed with reference to the ceiling mounted systems above, in environments where the ceiling is substantially higher than usual, the installation of such a system is very expensive and poses practical problems. In addition, as discussed with reference to the ceiling mounted systems above, such a system requires the use of extensive ceiling and floor structures in order to firmly secure the X-ray apparatus. Such systems are suitable in interventional procedures, however, as discussed with reference to the floor mounted systems above, they typically do not provide the full range of motion around several sides of the support table. Also, these systems require a track along one side of the patient support table, and the track and the ceiling support structure occupy substantial space along one entire side of the table. This restricts movement of clinical personnel where it might be critical for access, especially during emergency situations. It may also unnecessarily consume valuable operating space where required for additional equipment and/or personnel.

SUMMARY AND OBJECTS OF THE INVENTION

One of the objects of the present invention is to provide a treatment and imaging apparatus which does not require the use of ceiling mounting.

Another of the objects of the present invention is to provide an apparatus for treatment and imaging which has precise control over all motions including the ability to repeat an orientation from historical information.

Another of the objects of the present invention is to scan a stationary patient both longitudinally and laterally.

Another object of the present invention is to provide a floor mounted support mechanism for X-ray imaging apparatus that is placed into a position that does not interfere with operations within the room in which it is installed.

These and other objects of the present invention are provided for by an apparatus which has a support means for supporting a subject on a surface and an imaging means for imaging the subject. The imaging means is movably coupled to a guide means to allow relative movement of the imaging means about the support means. The guide means is located substantially along a plane which is substantially parallel to the surface of the support means. The support means may, in some embodiments, be rotatable from a horizontal to a vertical position for certain procedures. The guide means provides movement of the imaging means about at least three sides of the apparatus and, in some embodiments, is affixed to the floor. Further, the guide means is substantially aligned with a centerline of the support means. This provides a firm support for the imaging means, but keeps the support structure at a position where it will not interfere with clinical operations. The imaging means comprises, in one embodiment, an X-ray imager and receptor. In another embodiment, the imaging means may instead be used for treatment, wherein no receptor is required.

BRIEF DESCRIPTION OF DRAWINGS

The present invention is illustrated by way of example and not limitation in the figures of the accompanying in which like references indicate like elements and in which.

DETAILED DESCRIPTION

A fixed treatment and imaging apparatus is described. In the following description, for the purposes of explanation, specific mechanisms, materials, etc., are set forth in order to provide a thorough understanding of the present invention. It will be apparent, however, to one skilled in the art that the present invention may be practiced without these specific details. In other instances, well-known mechanisms and structures are discussed but not shown in order to not unnecessarily obscure the present invention.

Figure 1:
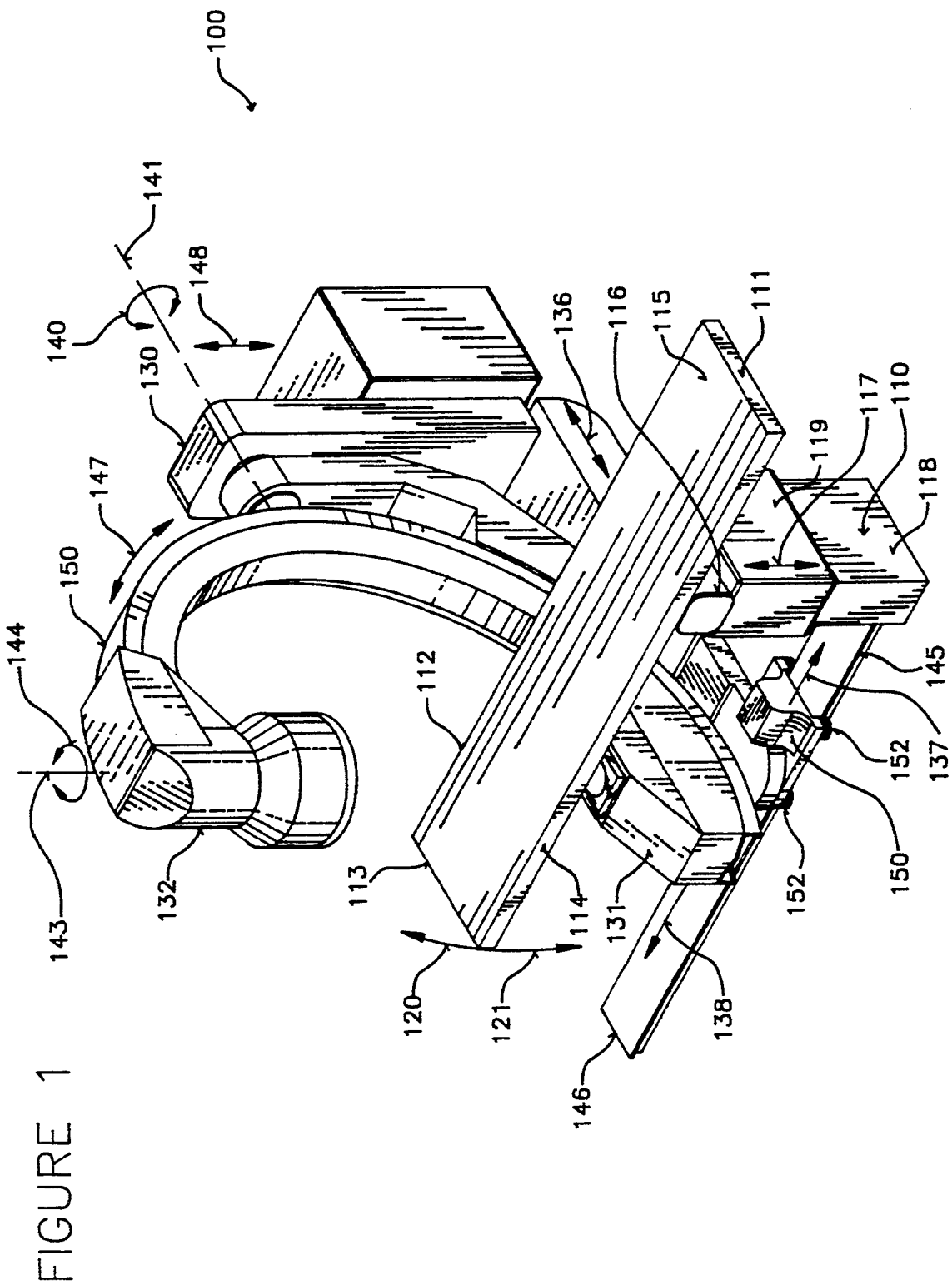
FIG. 1 shows a perspective view of the apparatus of the preferred embodiment as implemented with a horizontal patient support cantilever.

The preferred embodiment of the present invention is shown with reference to FIG. 1. Apparatus 100 of FIG. 1 comprises a cantilever support table 110 which is used to support subjects such as human patients during examination and/or treatment using apparatus 100. Further, 100 comprises an imaging apparatus unit 130 which has an X-ray emitter 131 and receptor 132 for generating images of the subject. In an alternative embodiment, the X-ray emitter may be utilized for treatment such as radiation therapy for treatment of cancer, in which case no receptor is required. Support cantilever 110 comprises an X-ray translucent support surface 115 upon which a subject may be placed. Support cantilever 110 has a rotatable hinge 116 upon which the surface may be rotated. The surface may be rotated in the directions shown generally as 120 and 121 in FIG. 1. Further, cantilever 110 comprises a height adjustment pedestal portion 118 which is affixed to the floor to provide a firm support for cantilever 110. In addition, cantilever 110 comprises a movable portion 119 upon which the remainder of the cantilever is supported, which comprises motorized gears and other mechanisms allowing height adjustment of the remainder of the cantilever in the directions shown generally as 117 in FIG. 1. In this manner, the cantilever may be raised and/or lowered according to the needs of the attending clinical personnel. Surface 115 is comprised of a carbon fiber or similar X-ray translucent material which allows imagery to be performed while the subject is resting upon the surface. Note that in alternative embodiments, such X-ray translucent material may not be required, depending upon the application.

Mechanisms contained within cantilever 110 comprise pulse width modulation servomotors which are controlled by a microprocessor in order to provide accurate control capabilities and the orientation of the tabletop 115. These include the ability to rotate in directions 120 and 121, and up and down for height adjustment in directions 117. Tabletop 115 of support cantilever 110 may be raised upright so that it is at a position 90° relative to the floor for certain applications including electrophysiology treatments of patients. While the patient is resting on support surface 115 in the horizontal position as shown in FIG. 1, the table may be raised to the 90° position. When rotated vertically, the patient may be held in place using straps or a footboard, depending on the application and environment.

Apparatus 100 further comprises an imaging apparatus 130 which comprises an X-ray emitter 131 and an X-ray receptor 132 for performing fluoroscopic studies of the subject. Note that 130, due to its unique construction, provides varying degrees of motion relative to the subject residing on cantilever 110. For instance, motorized orbital rotation 140 is provided about a transverse axis 141 for providing oblique imagery of the subject. In addition, 130 provides rotational motion in the directions shown as 147 of the C-arm unit 150 for providing various viewing angles around the longitudinal axis of the support surface 115. Also, height adjustment of 130 is possible as shown in directions 148 by mechanisms residing in unit 130. Further, motorized control of 130 is provided in the directions shown as 136, 137, and 138. Movement in the directions shown as 136 is provided transverse to the longitudinal axis of cantilever 110 to align the beam path at various positions in the subject's body. Further, lateral movement along a track 145 is provided in directions 137 and 138 for imagery of different portions along the longitudinal axis of support cantilever 110. For example, studies may be made of various venus or arterial systems along the length of a subject lying on the cantilever, such as the aorta or femoral arteries. This may be done by moving apparatus in directions 137 or 138 along track 145. Such movement is provided by servomotors contained within base unit 150 which drives wheels 152 for movement of 130 along track 145.

In addition, rotational motion of unit 130 about vertical axis 143 is provided in direction 144 about a pivot point contained within the base 150. Pivot axis 143, when imaging unit 130 is in the position shown in FIG. 1, is aligned with the beam path created by emitter 131. This rotational movement about the vertical axis 143 is provided under manual control in the preferred embodiment, however, movement about vertical axis 143 may be provided under motorized control in alternative embodiments. This rotational motion allows unit 130 to move along track 145 in direction 138, and once reaching the end 146 of track 145, to be rotated about axis 143 and back down track 145 in the direction shown as 137 in FIG. 1. This will provide imaging and movement of unit 130 along sides 112, 113, and 114 of support surface 115. This is a substantial improvement over prior an systems which only allowed movement along one side of the support surface. The alignment of track 145 along the centerline of support surface 115 this unique movement, which is discussed in more detail below.

Figure 2A:
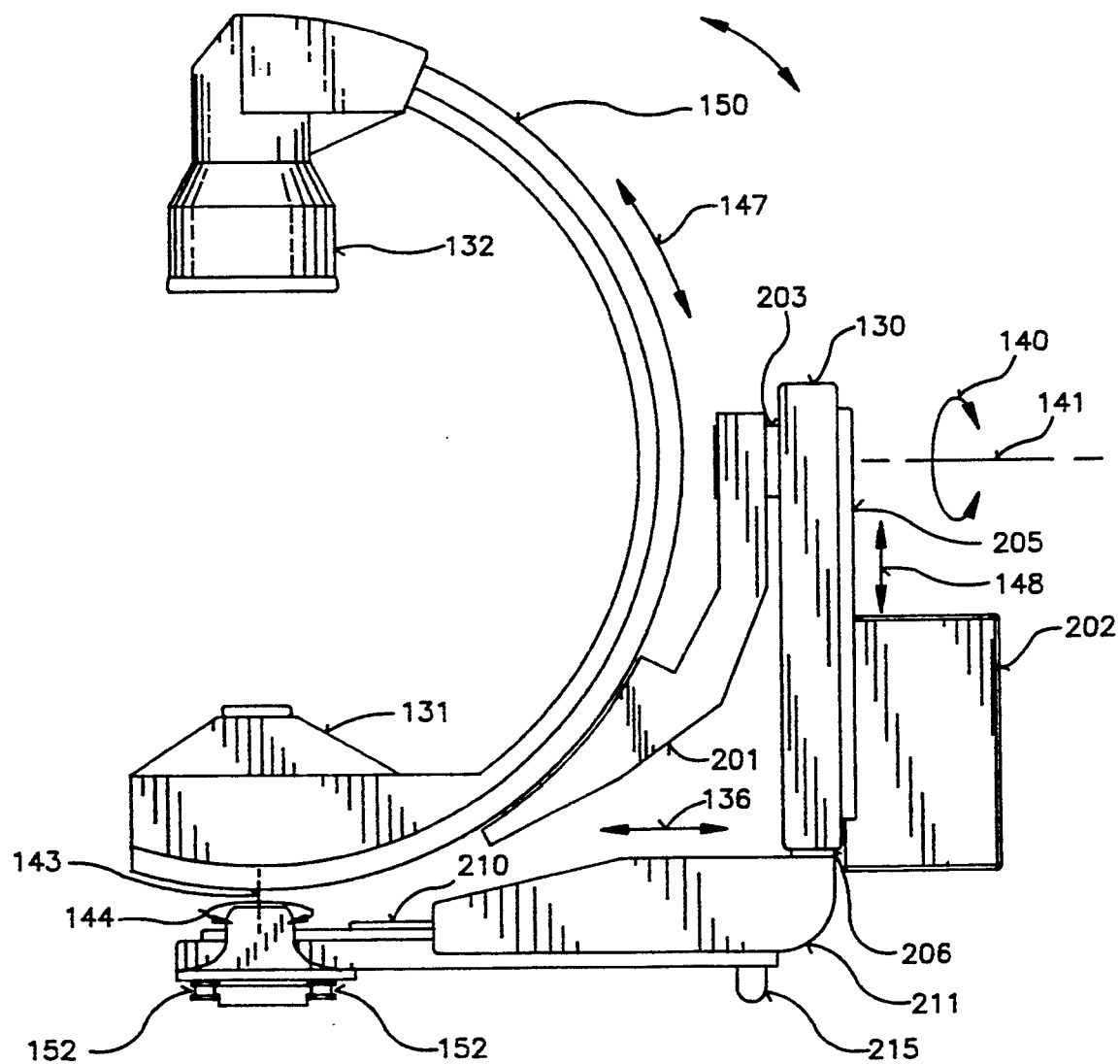
FIG. 2a shows a side view of the imaging apparatus and its various rotational motions.
Figure 2B:
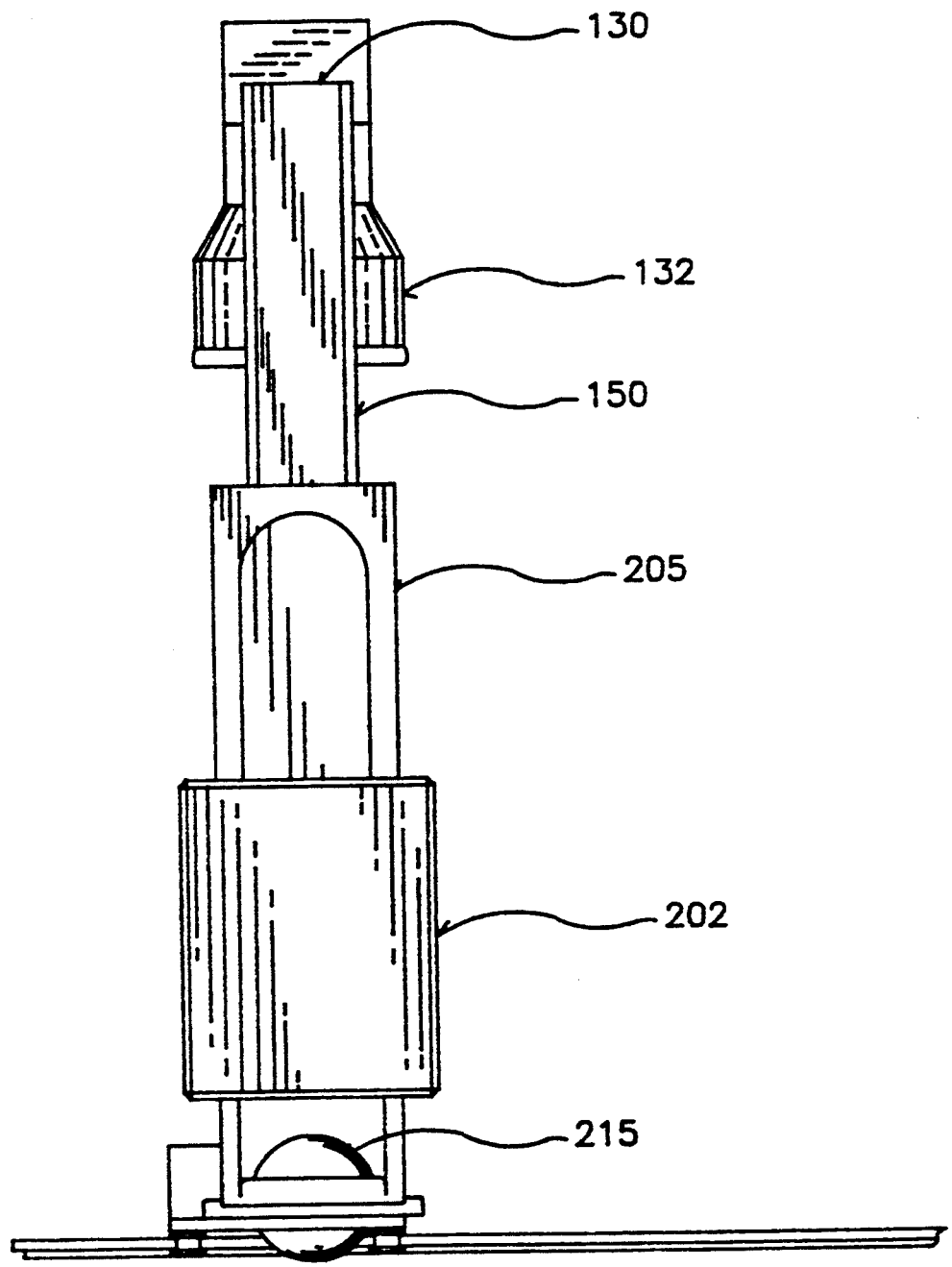
FIG. 2b shows a rear view of the imaging apparatus and the support track.

A side view of imaging apparatus 130 is shown in FIG. 2a. This shows additional structure which allows the movement of the imaging apparatus 130 in various directions. Note that the main support C-arm 150, which comprises X-ray emitter 131, and X-ray receptor 132 is mounted to an L-arm bracket 201 which provides the rotational motion about the longitudinal axis of the support surface 115 in directions 147. Note that the movement in directions 147 is motorized and achieved by the use of chain drive or similar means as was described in prior art systems such as Hollstein above. In addition, rotation about the transverse axis 141 is provided along directions 140 at pivot point 203 which is also under motorized control. Also shown in FIG. 2 is the generator enclosure 202 coupled to main support 205 of the L-arm imaging apparatus 130 which provides the necessary power generation for emitter 131 and receptor 132. Imaging apparatus 130 further comprises a track 210 upon which motorized units within base 211 provide motion transverse to the longitudinal axis of support surface 115 as indicated by arrows 136 shown in FIGS. 1 and 2a. Generator enclosure 202 further contains motorized units for providing height adjustment in the directions indicated by arrows 148. This allows the movement of the main support of the L-arm up and down along a support strut 206. Providing further support for the entire imaging apparatus is a wheel 215 which is coupled to rail 210 upon which the weight of imaging unit 130 is supported. Wheel 215 is shown in more detail from the rear of imaging apparatus 130 in FIG. 2b. This allows the rotational movement about vertical pivot axis 143 in directions 144 shown in FIGS. 1, 2a, and 3. This pivoting movement will be described now with reference to FIG. 3.

Figure 3:
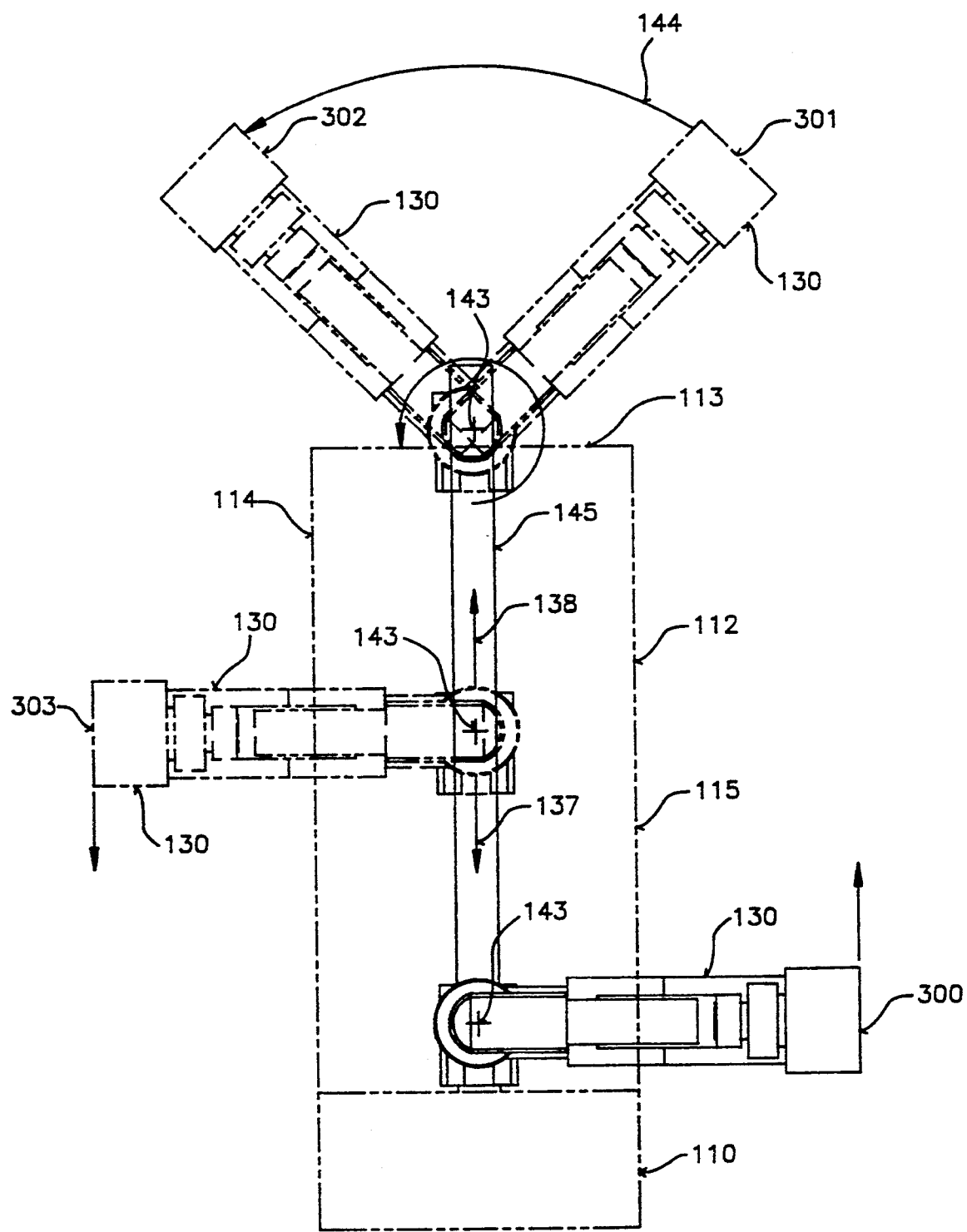
FIG. 3 shows a top view of the apparatus at various positions along the track.

A top view of the rotational motion and the movement of imaging unit 130 along track 145 is shown in FIG. 3. As is shown in FIG. 3, at a position 300, while residing at one end of track 145, the imaging apparatus 130 may be moved along the track in a direction 138 until it reaches the end position as shown in 301. Then, imaging unit 130 may pivot about axis 143 in the direction shown as 144 and thus come to a second position 302. Then, unit 130 may be moved along track 145 indirection 137 and thus come to position 303 along the second side of the table 114. Thus, using the mechanism provided at the pivot point 143, imaging unit 130 may provide imaging from sides 112, 113, and 114 of support surface 115. This imaging from at least three sides of the support cantilever provides for certain unique advantages not present in the prior art. Note that in the preferred embodiment, the pivoting about axis 143 is provided by a manual means, however, it can be appreciated by one skilled in the art that additional motorized units may be provided in the imaging apparatus 130 such that motorized pivoting about axis 143 may be provided. This has certain distinct advantages over the prior art apparatus such as providing clinical and equipment access to either side of the subject, providing imaging on either side, etc. Many advantages of this system can be appreciated by those skilled in the art.

One advantage of the use of servomotors in the present preferred embodiment is that of automated control by a control unit (such as a microprocessor). This may provide certain distinct improvements over the prior art such as the storage of position and orientation information of support 110 and imager 130 for duplication of scans at a later time. Therefore, a scan may be performed and duplicated later, providing the clinician with historical information to monitor a condition. This has certain distinct advantages over the prior art, such as Siczek, which do not have the capability to repeat scans accurately.

Figure 4:
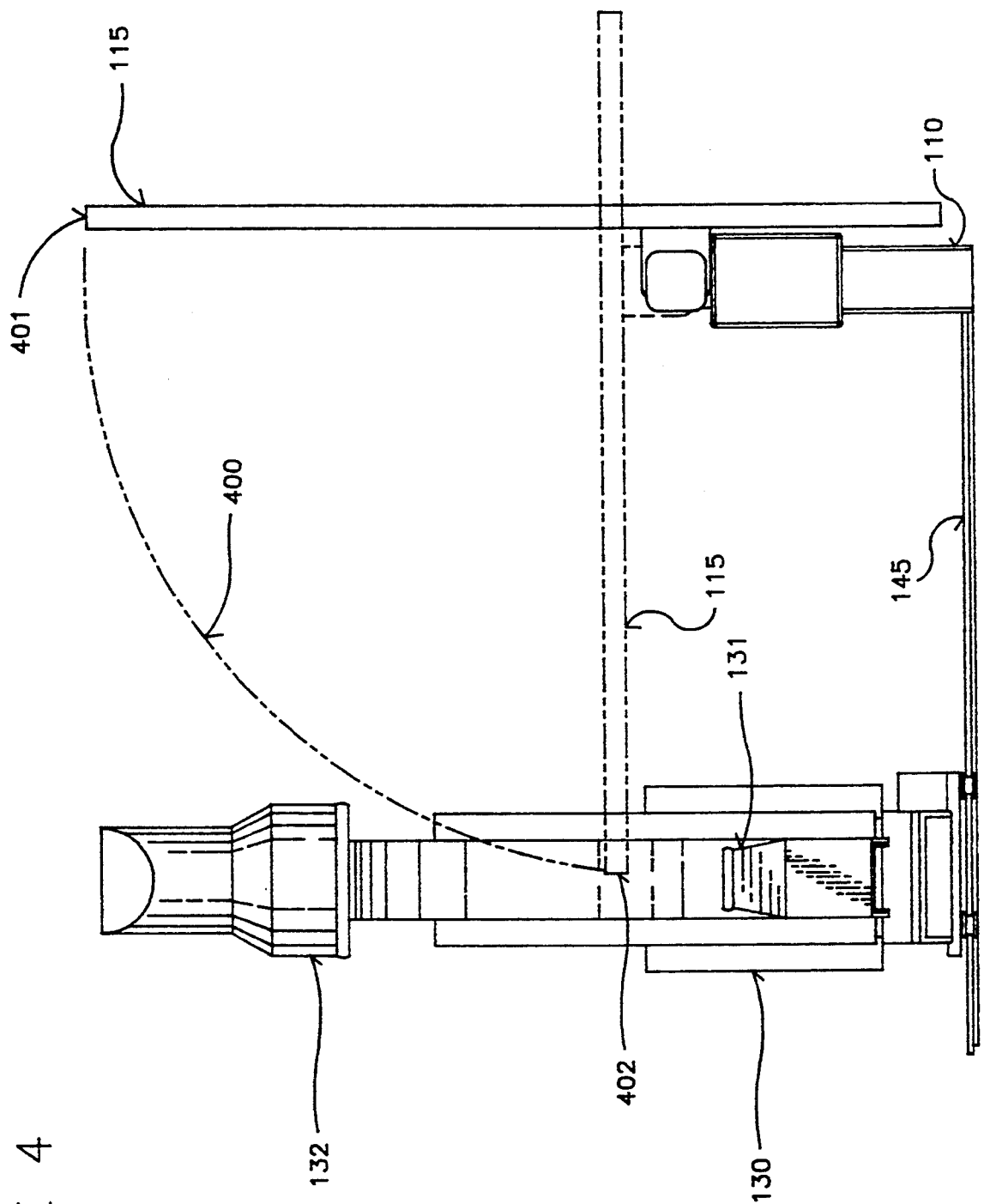
FIGS. 4 and 5 show various positions of the apparatus for prevention of collisions when raising or lowering a subject while resting on the support cantilever.

Envelope control of the positions of imaging unit 130 and surface 115 may also be provided by a control unit. This is so that during interventional procedures, precise rotation of cantilevers may be performed without collisions occurring between the cantilever support and the imaging unit 130. An interface between table 110 and imager 130 may be provided wherein servomotors position feedback is supplied to the control system to ascertain the current position of surface 115. For instance, in certain procedures, when medication is applied to the patient resting upon the support surface 115 in the vertical position shown as 401 shown in FIG. 4, if the patient develops syncope (fainting and/or an irregular heartbeat), the surface can be lowered immediately to the horizontal position 402 in order to prevent cardiac arrest. During this procedure, servomotors located in the motorized cantilever 110 may provide feedback to control mechanisms in order to ensure that collisions between the imaging apparatus 130 and cantilever support surface 115 do not occur. As shown in FIG. 4, the envelope 400 of the rotation of surface 115 does not intersect the position of the receptor head 132. Thus, depending on the orientation of either the imaging apparatus 130 and/or cantilever 115, control circuitry prevents collisions so that, in an emergency situation for example, the subject may be rotated to the horizontal position 402 from the vertical position 401 quickly. In the situation shown in FIG. 4, the imaging apparatus C-arm 130 may be moved automatically to the end of track 145 so that the rotation of support surface 115 supporting the patient does not strike receptor header 132.

Figure 5:
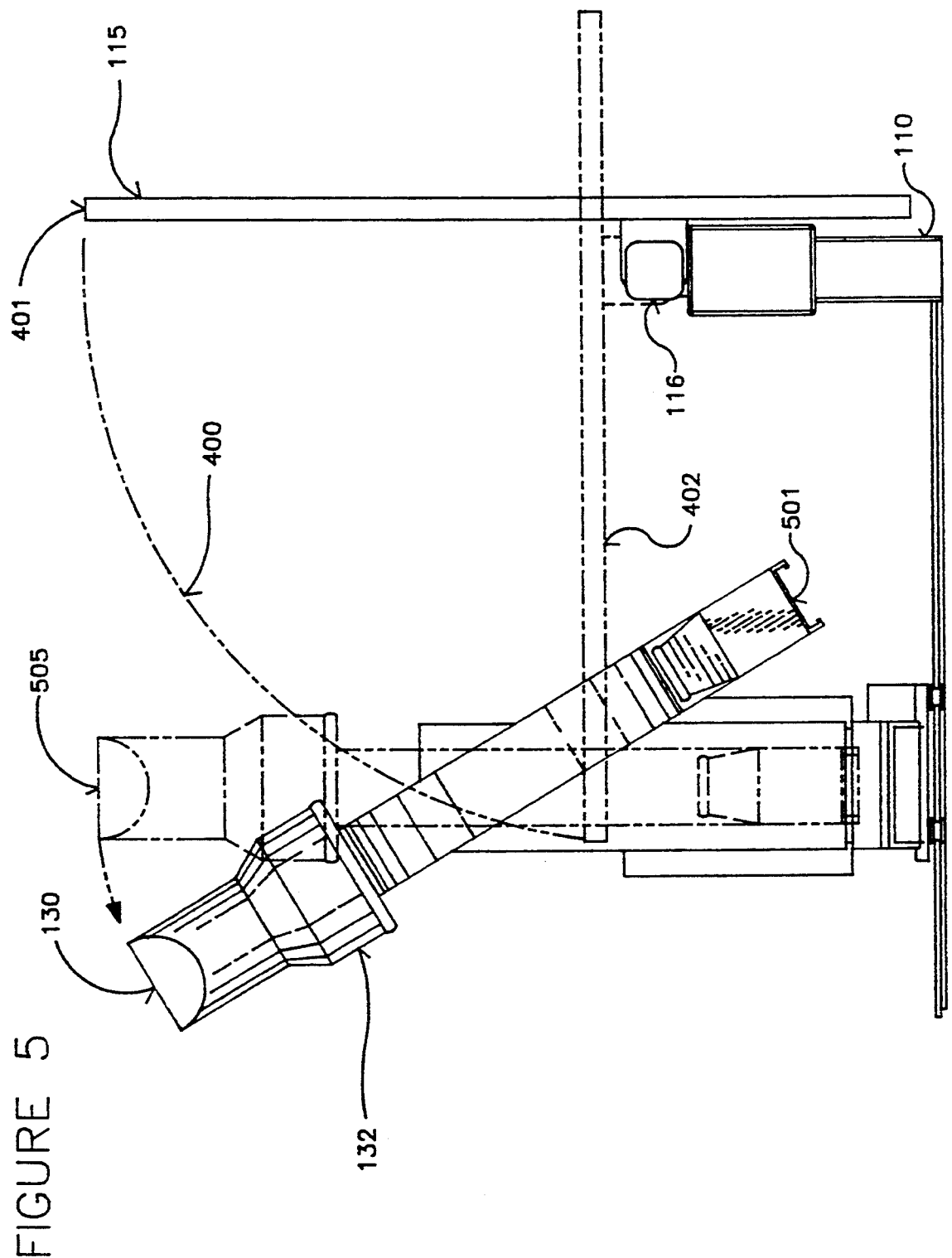

Another example of providing envelope control in order to prevent collisions between the cantilever surface 115 and the imaging apparatus 130 during interventional procedures is shown in FIG. 5. For instance, when the imaging apparatus 130 is in position 505, if the patient needs to be rotated back from vertical position 401 back to horizontal position 402, an envelope detection control can detect that imaging receptor head 132 will be in the path of surface 115, and thus the feedback provided by servomotors contained within the system will determine the positions. Thus, control circuitry contained within apparatus 100 may perform a maneuver such as a rotation to the position shown as 501 in FIG. 5, such that surface 115 will not strike receptor 132.

Figure 6:
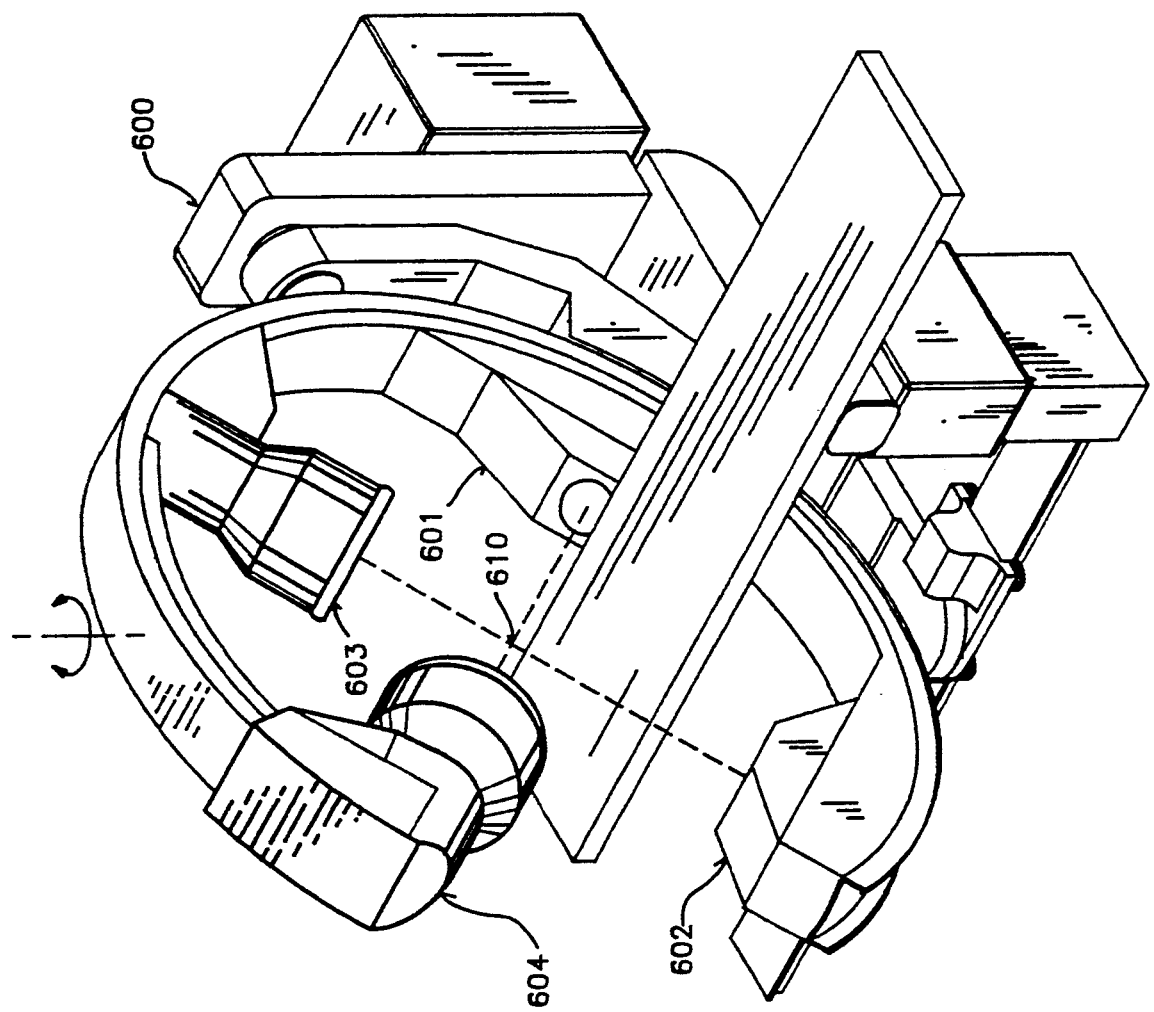
FIG. 6 shows an alternative embodiment of the present invention which utilizes two X-ray emitters and two X-ray receptors.

An alternative embodiment of the present invention is shown in FIG. 6. 600 of FIG. 6 comprises two X-ray emitters 601 and 602, and two X-ray receptors 603 and 604. The beams from the emitters thus have an intersection point 610 wherein objects within the subject may be triangulated. 600 comprises all the necessary pivot points and motorized controls in order to allow the same freedom of movement of the apparatus 100 shown in FIG. 1.

Figure 7:
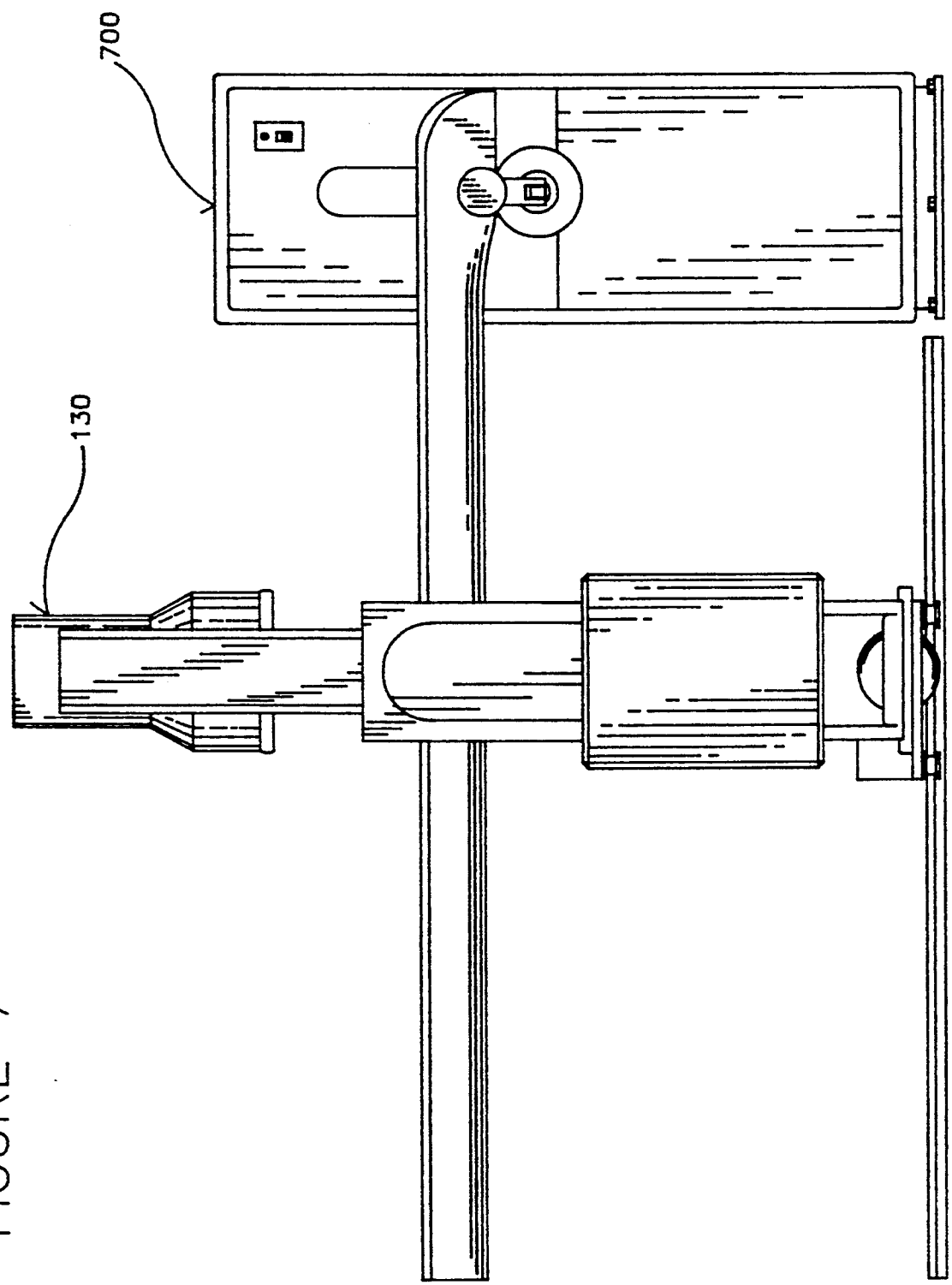
FIGS. 7 and 8 shown an alternative embodiment of the present invention which utilizes a patient support cantilever which is described in U.S. Ser. No. 07/616,677, entitled "A Patient Support Table," filed Nov. 21, 1990, now U.S. Pat. No. 5,131,105, issued Jul. 21, 1992, , of Harrawood et al., which is assigned to the assignee of the present invention.
Figure 8:
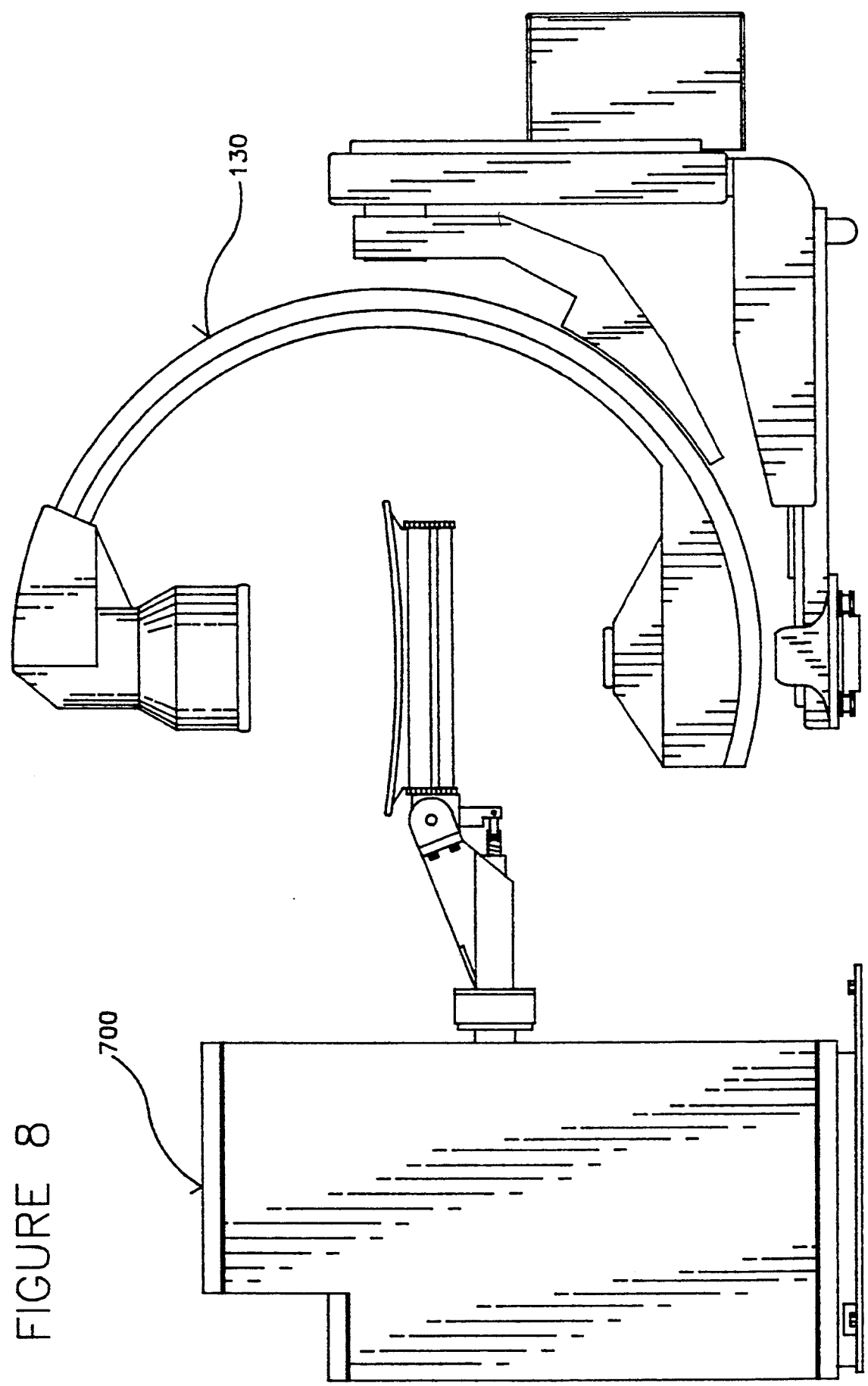

FIGS. 7 and 8 show yet another alternative embodiment of the present invention. In this embodiment, imaging apparatus 130 is shown in conjunction with another type of X-ray translucent imaging cantilever 700. FIG. 7 shows this apparatus in a side view and FIG. 8 shows this in a frontal view. Note that 700 shown in FIG. 7 is similar to the invention disclosed in U.S. patent application Ser. No. 07/616,677 entitled "A Patient Support Table," filed Nov. 21, 1990, now U.S. Pat. No. 5,131,105, issued Jul. 21, 1992, of Harrawood et al., and assigned to the assignee of the present invention. Note that the movable support apparatus 700 shown in FIGS. 7 and 8 has varying degrees of movement beyond that provided by the tables shown in FIGS. 1 through 6. Note also that in other alternative embodiments a floating tabletop typically used in angiographic procedures may also be used in conjunction with the imaging apparatus comprising a rail 145 as is disclosed in the present application.

In yet another alternative embodiment, recesses or channels may be provided in track 145 (not shown) in order to retain the cabling for power and control wiring which is required for system 100. Besides aesthetic advantages, this may have the advantage that the cables do not interfere with treatment or other clinical procedures, and the movement of the apparatus. Other advantages will be appreciated by those skilled in the art.

Thus, an affixed imaging system which mounted on a track parallel with a support apparatus has been described. In the foregoing specification, the present invention has been described with reference to specific embodiments thereof. It will, however, be evident that various modifications and changes may be made thereto without departing from the broader spirit and scope of the present invention as set forth in the appended claims. The specification and drawings are, accordingly, to be regarded in an illustrative rather than a restrictive sense.

What is claimed is:

1. An apparatus comprising:
   a. support means for supporting a subject on a surface thereof, said support means having at least one axis of rotation;
   b. imaging means for imaging said subject; and
   c. guide means coupled with said imaging means for allowing relative movement of said imaging means about said support means, said guide means aligned with a centerline of said surface and in a plane which is substantially parallel to and beneath said surface of said support means.

2. An apparatus for examination of a subject comprising:
   a. support means having a surface for supporting said subject;
   b. a single guide means mounted along a plane parallel to said surface and substantially aligned along with a centerline of and beneath said surface, said guide means for guiding an imaging means; and
   c. imaging means movably coupled to said guide means for imaging said subject from opposite lateral sides of said support surface.

3. The apparatus of claim 2 wherein said imaging means comprises an X-ray emitter.

4. The apparatus of claim 3 wherein said imaging means further comprises an X-ray collector, said X-ray collector positioned to receive X-rays emitted by said X-ray emitter.

5. The apparatus of claim 2 wherein said support means further comprises a support structure, said support structure extending beneath said support surface.

6. The apparatus of claim 5 wherein said support structure comprises a rotation means for rotating said support means about an axis of rotation from a horizontal position to a vertical position.

7. The apparatus of claim 6 wherein said guide means extends beyond one end of said support surface a distance which is sufficient to allow movement of said imaging means beyond said one end of said support surface.

8. The apparatus of claim 2 wherein said guide means is coupled to the floor.

9. The apparatus of claim 2 wherein movement of said imaging means is controlled by servomotors.

10. The apparatus of claim 2 wherein said apparatus provides relative movement of said imaging means along an axis perpendicular to said plane.

11. The apparatus of claim 2 wherein said guide means comprises a channel for accommodating cabling for said imaging means.

12. An imaging apparatus comprising:
   a. a support means having a top surface for supporting a patient; and
   b. an imaging means movably coupled relative to said support means along a guide means, where said guide means is located on a ground floor and is substantially aligned with a centerline of said top surface.

13. The imaging apparatus of claim 12 wherein said imaging means is movably coupled relative to said support means allowing said imaging means to move substantially along at least two sides of said support means.

14. The imaging apparatus of claim 13 wherein said imaging means is movably coupled to allow movement along at least three sides of said support means.

15. An apparatus comprising:
   a. support means allowing for accommodation of a body, such as a human body, on a surface thereof, said support means having a central axis:
   b. imaging means for imaging said body; and
   c. guide means coupled with said imaging means for allowing relative movement of said imaging means about opposite sides of said support means, wherein said guide means is located below and is substantially parallel to said surface of said support means and is aligned with said central axis of said support means.

16. A floor-mounted X-ray imaging apparatus allowing for imaging of a patient on a support table, said support table having lateral sides and opposing ends and having a surface, said X-ray imaging apparatus movably coupled to a track substantially aligned with a centerline of and located beneath said surface of said support table to allow movement of said X-ray imaging apparatus about at least said lateral sides and one of said opposing ends of said table.

17. The floor-mounted X-ray apparatus of claim 16 further coupled to provide for relative movement away from and toward said support table.

18. The X-ray apparatus of claim 16 wherein said X-ray apparatus is coupled along a floor-mounted track.

19. An apparatus for imaging a subject comprising:
   a. a support means for supporting the subject, the support means being substantially rectangular and located in a first plane; and
   b. an imaging means for imaging the subject located adjacent to said support means, the imaging means being coupled to a coupling means which is affixed to the floor, the coupling means being oriented substantially parallel to the first plane and aligned along a centerline of said support means, said coupling means allowing said imaging means to traverse and rotate about at least two lateral sides and one end of said support means.

20. The apparatus of claim 19 wherein said imaging means comprises an X-ray emitter and receptor.

21. The apparatus of claim 19 wherein said imaging means comprises a C-arm X-ray unit.

22. The apparatus of claim 19 wherein the imaging means comprises two sets of X-ray emitters and receptors which have beam paths converging at the centerline of said support means.

23. The apparatus of claim 19 further comprising an envelope control means which prevents said imaging means from colliding with the support means.

24. The apparatus of claim 19 wherein the imaging means comprises an longitudinal axis of rotation and a lateral axis of rotation.

25. The apparatus of claim 19 wherein the support means comprises an angiographic support surface.

26. The apparatus of claim 19 wherein the support means comprises a floating examination table.

27. An apparatus for examination of a human body comprising:
   a. support means having a surface for supporting said human body;
   b. guide means located parallel and aligned along a centerline of and located beneath said surface, said guide means for guiding an imaging means; and
   c. imaging means movably coupled with said guide means for imaging said body.

28. The apparatus of claim 27 wherein said guide means defines a channel for accommodating cabling providing for coupling of said imaging means with external sources.

29. The apparatus of claim 28 wherein said external sources comprise power sources.

30. The apparatus of claim 28 wherein said external sources comprises control means for controlling said imaging means.

31. The apparatus of claim 27 wherein said support means has a first side and a second side, said first and second sides located opposite each other, said guide means extending beyond said first side.

32. The apparatus of claim 31 wherein said support means is movable about an axis of rotation.

33. The apparatus of claim 32 wherein said guide means extends beyond said first side at least enough to allow movement of said imaging means beyond said fast side.

34. The apparatus of claim 27 wherein said guide means is located on the floor.

35. The apparatus of claim 27 wherein movement of said imaging means is provided by motors.

36. The apparatus of claim 27 wherein said apparatus provides relative movement of said imaging means along an axis perpendicular to said plane.

37. The apparatus of claim 27 wherein said imaging means comprises an X-ray emitter.

38. The apparatus of claim 27 wherein said imaging means further comprises an X-ray collector, said X-ray collector positioned to receive X-rays emitted by said X-ray emitter.

39. An imaging apparatus comprising:
   a. a support means having a top surface for supporting a patient; and
   b. an imaging means movably coupled relative to said support means along a guide means, wherein said guide means is located on a ground surface, said ground surface being below said top surface, and wherein said guide means is aligned with a centerline of said top surface.

40. The imaging apparatus of claim 39 wherein said imaging means is movably coupled relative to said support means allowing said imaging means to move substantially along at least two sides of said support means.

41. The imaging apparatus of claim 40 wherein said imaging means is movably coupled to allow movement along at least three sides of said support means.

42. An apparatus comprising:
   a. a support assembly having a surface for supporting a subject;
   b. an imaging assembly for imaging said subject; and
   c. a guide substantially aligned along a centerline of and located beneath said surface, said guide coupled to said imaging assembly for guiding said imaging assembly.

43. The apparatus of claim 42 wherein said guide is located on a floor.

44. The apparatus of claim 42 wherein said guide is located in a plane substantially parallel to said surface and wherein said apparatus provides relative movement of said imaging assembly along an axis perpendicular to said plane.

45. The apparatus of claim 42 wherein said support assembly comprises a rotation assembly for rotating said surface about an axis of rotation from a substantially horizontal position to a substantially vertical position.

46. The apparatus of claim 42 wherein said guide allows said imaging assembly to move substantially along at least two sides of said surface.

47. The apparatus of claim 46 wherein said guide allows said imaging assembly to move substantially along at least three sides of said surface.

48. The apparatus of claim 42 wherein said imaging assembly comprises an X-ray emitter.

49. The apparatus of claim 48 wherein said imaging assembly further comprises an X-ray collector, said X-ray collector positioned to receive X-rays emitted by said X-ray emitter.

50. The apparatus of claim 42 wherein said surface of said support assembly has a first side and a second side, said first and second sides located opposite each other, said guide extending beyond said first side.

51. The apparatus of claim 50 wherein said surface of said support assembly is movable about an axis of rotation.

52. The apparatus of claim 51 wherein said guide extends beyond said first side a distance which is sufficient to allow movement of said imaging assembly beyond said first side.

53. The apparatus of claim 42 wherein said guide includes a track.

* * * * *